(12) United States Patent
Ishii et al.

(10) Patent No.: US 6,833,004 B2
(45) Date of Patent: Dec. 21, 2004

(54) STENT

(75) Inventors: Naoki Ishii, Kanagawa (JP); Hideyuki Togawa, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 152 days.

(21) Appl. No.: 10/188,969

(22) Filed: Jul. 5, 2002

(65) Prior Publication Data

US 2003/0033004 A1 Feb. 13, 2003

(30) Foreign Application Priority Data

Jul. 6, 2001 (JP) .................................. 2001-206665

(51) Int. Cl.$^7$ ................................. A61F 2/06
(52) U.S. Cl. .................. 623/1.15; 623/1.42; 623/143
(58) Field of Search ............................. 623/1.13, 1.21, 623/1.2, 1.39–1.48, 1.44–1.47, 117; 606/108, 191–194, 195, 198

(56) References Cited

U.S. PATENT DOCUMENTS

| | | | | |
|---|---|---|---|---|
| 5,092,841 A | * | 3/1992 | Spears | 604/103.01 |
| 5,242,451 A | | 9/1993 | Harada et al. | |
| 5,447,724 A | | 9/1995 | Helmus et al. | |
| 5,507,767 A | | 4/1996 | Maeda et al. | |
| 5,534,287 A | | 7/1996 | Lukic | |
| 5,632,771 A | | 5/1997 | Boatman et al. | |
| 5,662,713 A | | 9/1997 | Andersen et al. | |
| 5,700,286 A | * | 12/1997 | Tartaglia et al. | 623/1.15 |
| 5,733,303 A | | 3/1998 | Israel et al. | |
| 5,855,598 A | * | 1/1999 | Pinchuk | 623/1.13 |
| 5,865,814 A | * | 2/1999 | Tuch | 623/1.15 |
| 5,888,201 A | | 3/1999 | Stinson et al. | |
| 6,042,875 A | | 3/2000 | Ding et al. | |
| 6,099,562 A | * | 8/2000 | Ding et al. | 623/1.46 |
| 6,379,379 B1 | * | 4/2002 | Wang | 623/1.15 |

FOREIGN PATENT DOCUMENTS

| | | |
|---|---|---|
| EP | 0 623 354 A1 | 11/1994 |
| EP | 0 734 721 A2 | 10/1996 |
| EP | 0 747 069 A2 | 12/1996 |
| EP | 0 910 998 A2 | 4/1999 |
| JP | 4-68939 B2 | 11/1992 |
| JP | 7-529 A | 1/1995 |
| JP | 7-500272 A | 1/1995 |
| JP | 8-33718 A | 2/1996 |
| JP | 8-502428 A | 3/1996 |
| JP | 8-507243 A | 8/1996 |
| JP | 9-99056 A | 4/1997 |
| JP | 9-215753 A | 8/1997 |
| JP | 10-50367 A | 4/1998 |
| JP | 11-221288 A | 8/1999 |
| JP | 2000-501328 A | 2/2000 |
| WO | WO 98/14137 A1 | 4/1998 |
| WO | WO 00/45744 A1 | 8/2000 |

* cited by examiner

*Primary Examiner*—Julian W. Woo
*Assistant Examiner*—Victor Nguyen
(74) *Attorney, Agent, or Firm*—Burns, Doane, Swecker & Mathis, L.L.P.

(57) ABSTRACT

A stent wherein a biologically/physiologically active substance is loaded on the stent main body is provided. The active substance is gradually released for a prolonged period without being rapidly released in a short period. The stent comprises a stent main body, and a sustained release coating formed on the stent main body; wherein the coating comprises a biologically/physiologically active substance layer formed on the stent main body, and a polymer layer formed on the biologically/physiologically active substance layer; and the biologically/physiologically active substance layer comprises at least one biologically/physiologically active substance; the polymer layer comprises a vapor or water-permeable polymer, and a water-swellable substance dispersed in the polymer and swollen by absorption of the vapor or the water; and cracks are formed in the polymer layer when the water-swellable substance is swollen by absorbing the vapor or the water.

18 Claims, 9 Drawing Sheets

STENT

BACKGROUND OF THE INVENTION

1. Field of the Invention

This invention relates to a stent which is implanted in a stenotic or occluded lesion of a body duct such as blood vessel, bile duct, trachea, esophagus, or urethra in order to maintain the opening of the lesion. More specifically, this invention relates to a stent which is capable of maintaining the opening of the lesion for a prolonged period by sustained release of a biologically/physiologically active substance from the stent surface, namely, by the gradual and slow release of such substance which has the effect of suppressing the restenosis.

2. Description of the Related Art

Angioplasty which is conducted in the case of ischemic heart disease is described as one typical example.

With the westernization of dietary habits in our country, the number of patients suffering from ischemic heart diseases (angina pectoris, cardiac infarction) has sharply increased. In order to treat the heart diseases, percutaneous transluminal coronary angioplasty (PTCA) has been developed and the number of cases where PTCA is applied has dramatically increased. Today, technological development has enabled application of the PTCA in a variety of cases, and the PTCA is applied not only to the cases where PTCA was originally applied namely, not only to the circumscribed lesion (with short lesion length) or the single vessel lesion (with the stenosis only at one vessel) but also to the cases wherein the lesion is located at a more distal site, eccentric, and calcined, or to the cases of multivessel lesion (with the stenosis at two or more vessels). PTCA is a procedure wherein a small incision is made in the artery in the thigh or arm of the patient to leave the introducer sheath in the incision; a guidewire is first introduced through the lumen of the introducer sheath; a hollow tube called a guide catheter is inserted in the blood vessel and over the guidewire to place the guide catheter at the entrance of the coronary artery; the guidewire is withdrawn; another guidewire and a balloon catheter is inserted in the lumen of the guide catheter and the balloon catheter is advanced through the coronary artery of the patient after the guidewire and under the X-ray radiography to the lesion, namely to the stenotic or occluded lesion of the blood vessel to place the balloon catheter at the lesion; and the balloon is inflated at this lesion at the predetermined pressure for 30 to 60 seconds for once or for several times by the physician. By this procedure, the inner cavity of the blood vessel at the site of the lesion is opened, and this opening is maintained. As a consequence, amount of blood flowing through the blood vessel becomes increased. However, intimal thickening occurs as the wound healing of the vascular wall in the case, for example, when wounds are made in the vascular wall by the catheter, and restenosis is reported in 30 to 40% of the PTCA cases.

There is no established method for preventing the restenosis. However, use of the stent, atherectomy catheter, and other device has been investigated, and these methods are starting to gain some results. The term "stent" used herein designates a hollow medical device which is implanted in the stenotic or occluded lesion of a blood vessel or other body duct to open the lesion and to maintain the opening for treating various diseases caused by such stenosis or occlusion of the body duct. A stent is a medical device which usually comprises a metal material or a polymer material, and various stents have been proposed. Exemplary such stents include those wherein small slots are formed on the side wall of the hollow tubular body of metal or polymer material, and those produced by braiding a metal wire or a polymer fiber into a cylindrical shape. A stent is implanted for the purpose of preventing or reducing the risk of the restenosis that may take place after the PTCA and other procedures. However, it has so far been unsuccessful to significantly prevent the restenosis by using the stent alone.

Recently, various attempts for reducing the occurrence of the restenosis have been made by loading the stent with various biologically/physiologically active substances such as a carcinostatic for local and sustainedly releasing the biologically/physiologically active substance at the lesion where the stent has been implanted. For example, JP 8-33718 A proposes a stent wherein a mixture of a therapeutical substance (biologically/physiologically active substance) and a polymer is coated on the surface of the stent main body, and JP 9-99056 A proposes a stent wherein a bioactive material layer (biologically/physiologically active substance layer) is formed on the surface of the stent main body, and a polymeric porous material layer is formed on the surface of the bioactive material layer.

However, in the case of the stent proposed in JP 8-33718 A, the therapeutic substance (biologically/physiologically active substance) is incorporated in the polymer, so that the stent is associated with the problem of decomposition and degradation of the biologically/physiologically active substance due to the chemical action with the polymer, that is, with the problem of the stability of the biologically/physiologically active substance. For example, when the polymer selected is polylactic acid, this polymer has the characteristic feature that it generates an acid upon its decomposition despite its favorable unique function that it is decomposable in the body and enables the release of the biologically/physiologically active substance. When an acid-sensitive substance is selected for the biologically/physiologically active substance, the decomposition of the polylactic acid will create the problem of the decomposition and degradation of the biologically/physiologically active substance. In addition, when the polymer selected has a high decomposition speed in the body, release of the biologically/physiologically active substance will be completed in a short period (within several days after the implantation) and the stent will suffer from the problem of insufficient suppression of the restenosis of the vascular wall. As a consequence, the stent of the type proposed in JP 8-33718 A is associated with the problem of limited combination of the polymer and the biologically/physiologically active substance used in the stent in view of preventing the decomposition and degradation of the biologically/physiologically active substance, and at the same time, in view of securing a reliable release of the biologically/physiologically active substance for a prolonged period (for several weeks to several months after the stent implantation).

On the other hand, in the case of the stent proposed in JP 9-99056 A, the bioactive material layer (biologically/physiologically active substance layer) and the polymer layer are formed as different layers, so that this stent is free from the risk of the decomposition and degradation of the biologically active substance by the action with the polymer. In this stent, however, the polymer layer covering the biologically/physiologically active substance comprises a porous material wherein passages are defined from one surface to the other surface of the polymer layer, and the biologically/physiologically active substance layer is exposed to the outer atmosphere of the stent (atmosphere outside the polymer layer) from the time of its production.

Therefore, the stent of such structure is associated with the risk that the biologically/physiologically active substance is released through the passages present in the porous material before implanting the stent in the body. The stent of this type is also associated with the risk after implanting the stent in the lesion, namely, with the risk of the phenomenon that the biologically/physiologically active substance is rapidly released in a short period (within several days after the implantation), that is, the initial burst, and this stent suffered from the difficulty of sustained release of the biologically/physiologically active substance, namely, slow, gradual release of the biologically/physiologically active substance for a prolonged period (for several weeks to several months after the implantation).

SUMMARY OF THE INVENTION

In view of the situation as described above, an object of the present invention is to provide a stent wherein the biologically/physiologically active substance can be stably loaded on the stent main body without undergoing decomposition or degradation, and at the same time, wherein sustained release of the biologically/physiologically active substance, namely, slow, gradual release of the biologically/physiologically active substance for a prolonged period with no rapid release of the biologically/physiologically active substance is enabled once the stent is implanted in the lesion.

Such objects are attained by the present invention as described in the following (1) to (9).

(1) A stent to be implanted in a body duct comprising
  a cylindrical stent main body extending in axial direction and having an opening on each end of the axially extending stent main body and
  a sustained release coating formed on the surface of the stent main body from which a biologically/physiologically active substance is released; wherein
    said sustained release coating comprises
    a layer of the biologically/physiologically active substance formed on the surface of said stent main body, and
    a polymer layer formed on said biologically/physiologically active substance layer to cover said biologically/physiologically active substance layer; and
  said biologically/physiologically active substance layer comprises at least one biologically/physiologically active substance;
  said polymer layer comprises a vapor or water-permeable polymer, and a water-swellable substance dispersed in said polymer and swollen by absorption of the vapor or the water; and
  cracks are formed in said polymer layer when said water-swellable substance is swollen by absorbing the vapor or the water, and the biologically/physiologically active substance in said biologically/physiologically active substance layer is released to the exterior of said sustained release coating through said polymer layer.
(2) A stent according to the above (1) wherein said stent main body comprises a metal material.
(3) A stent according to the above (1) wherein said stent main body comprises a polymer material.
(4) A stent according to any one of the above (1) to (3) wherein said biologically/physiologically active substance layer comprises solely from the biologically/physiologically active substance.
(5) A stent according to any one of the above (1) to (3) wherein said biologically/physiologically active substance layer comprises the biologically/physiologically active substance and an additional component which imparts tackiness to said biologically/physiologically active substance layer.
(6) A stent according to any one of the above (1) to (5) wherein said biologically/physiologically active substance is at least one member selected from a carcinostatic, an immunosuppressive, an antibiotic, an antirheumatic, an antithrombotic, an antihyperlipidemic, an ACE inhibitor, a calcium antagonist, an integrin inhibitor, an antiallergic, an antioxidant, a GPIIb/IIIa antagonist, retinoid, flavonoid, carotenoid, a lipid improving agent, a DNA synthesis inhibitor, a tyrosine kinase inhibitor, an antiplatelet, a vascular smooth muscle antiproliferative agent, an antiinflammatory agent, a biological material, an interferon, and a NO production accelerator.
(7) A stent according to any one of the above (1) to (6) wherein said vapor or water-permeable polymer constituting the polymer layer is a member selected from silicone polymer, cellulose polymer, polyurethane, polyester, vinyl polymer, acrylic polymer, and thermoplastic elastomer.
(8) A stent according to any one of the above (1) to (7) wherein said water-swellable substance is a low molecular weight salt having a molecular weight of up to 1000.
(9) A stent according to the above (8) wherein said low molecular weight salt is a salt which is found in a body.
(10) A stent according to the above (8) or (9) wherein said low molecular weight salt is sodium chloride.

DETAILED DESCRIPTION OF THE INVENTION

Figure 1:
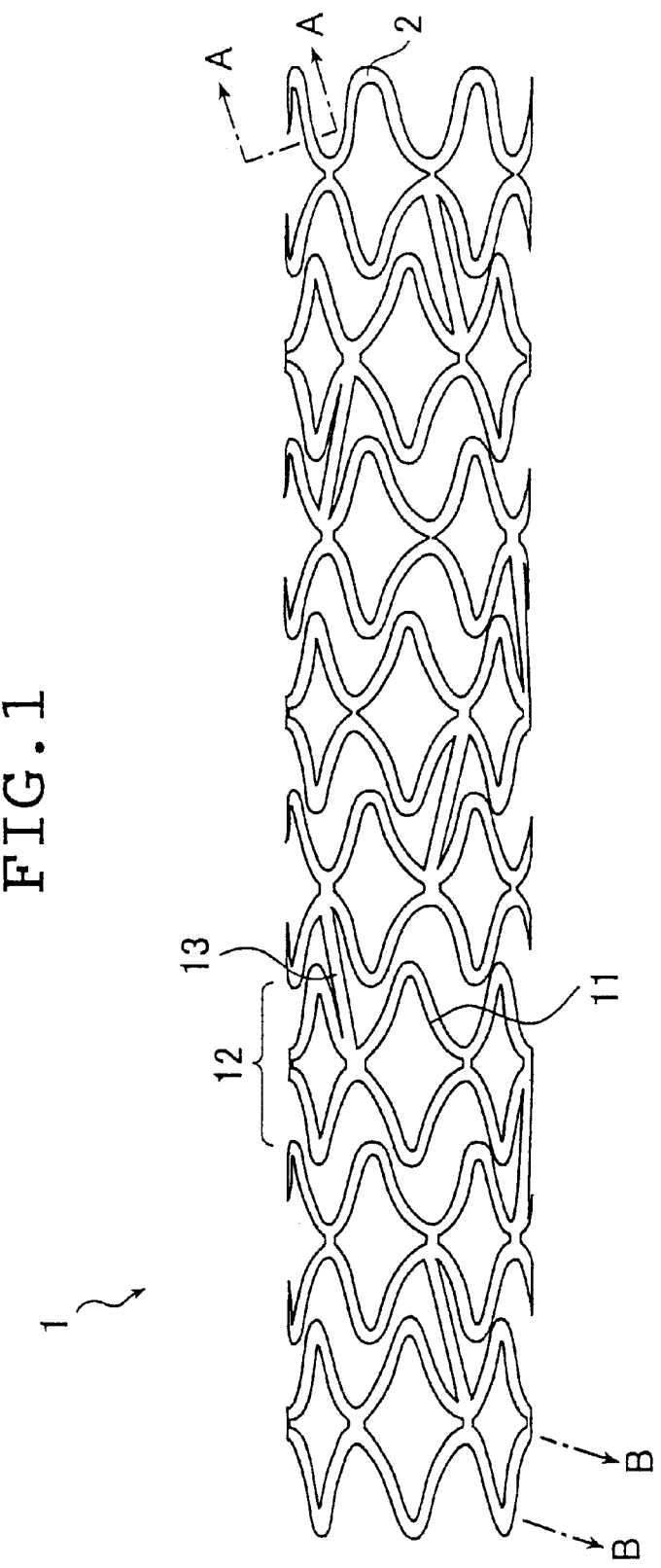
FIG. 1 is an elevational view showing the stent according to an embodiment of the present invention.

Next, the stent of the present invention is described in detail by referring to the preferred embodiments shown in the drawings.

The stent of the present invention comprises a stent main body and a sustained release coating formed to cover the surface of the stent main body.

Figure 2:
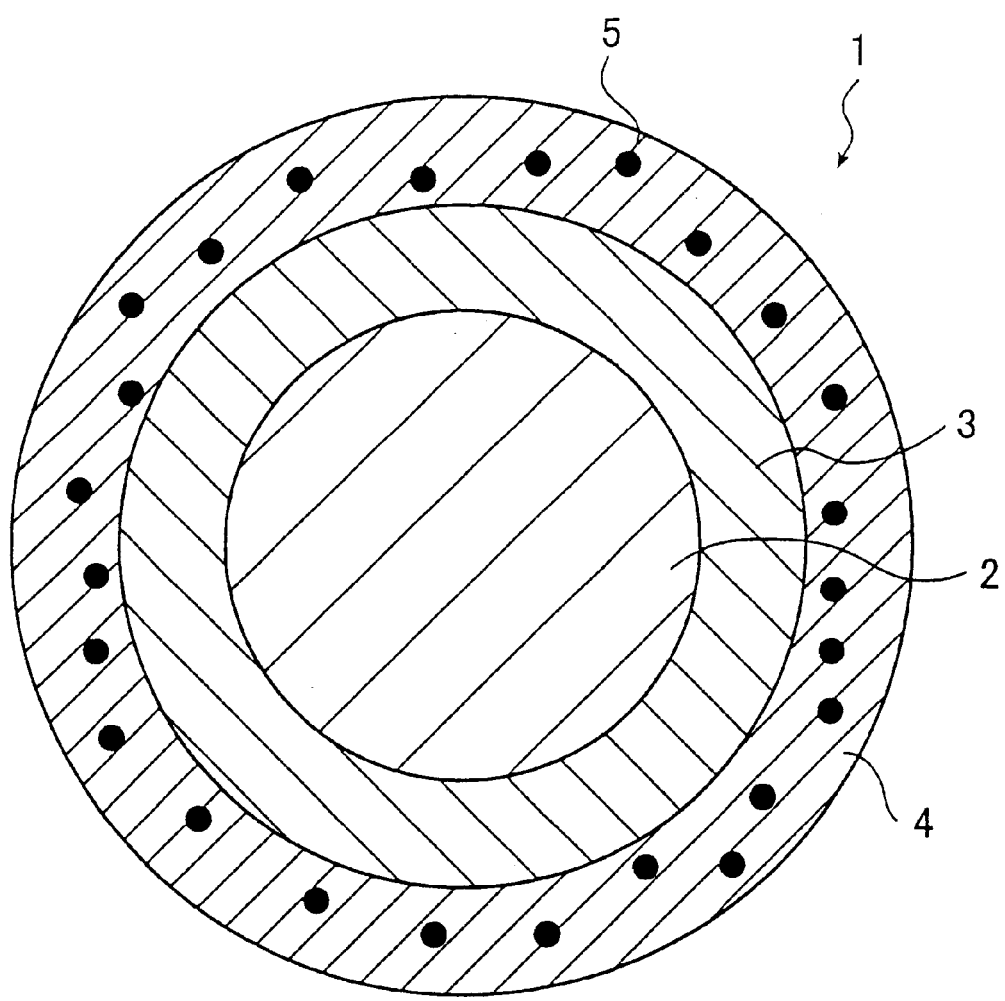
FIG. 2 is an exploded transverse cross-sectional view taken along lines A—A in FIG. 1.
Figure 3:
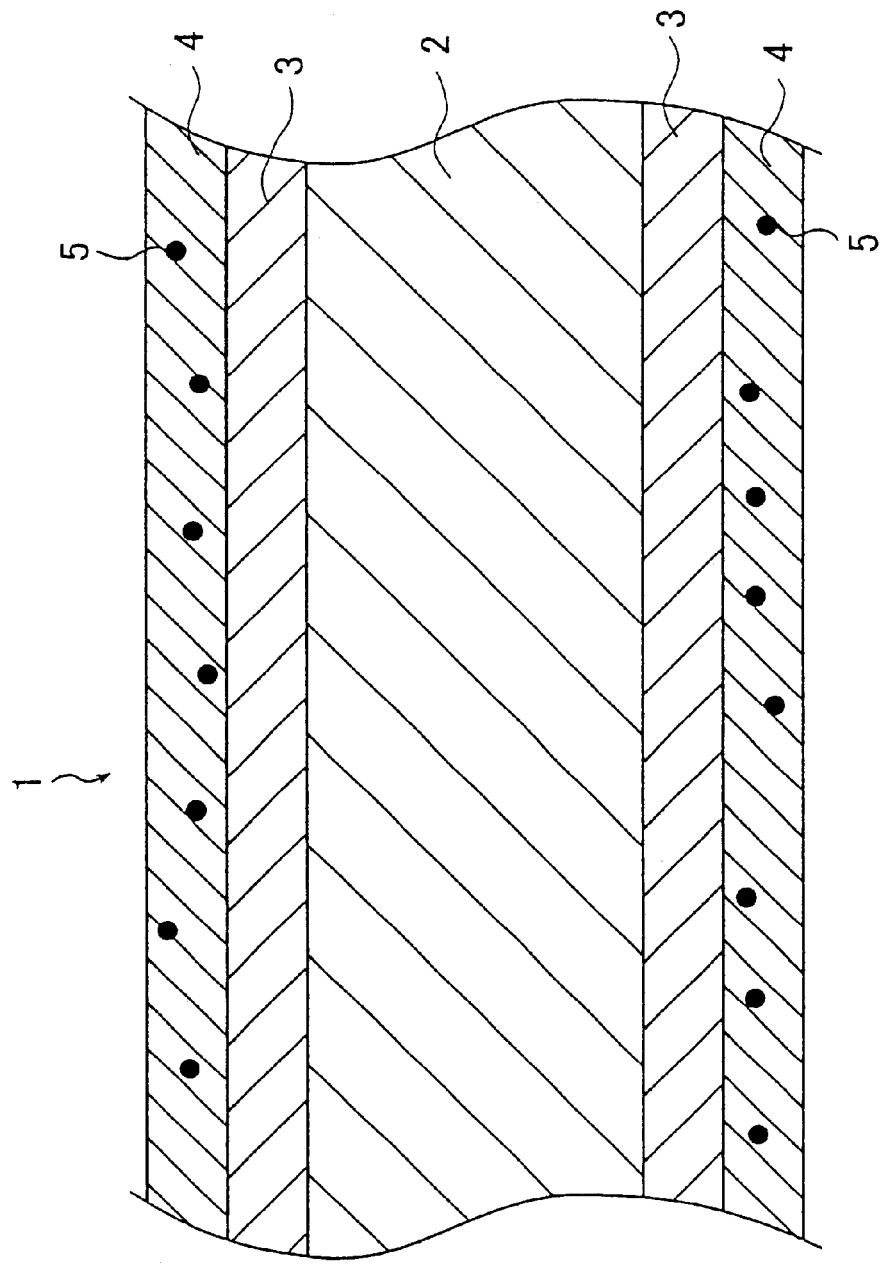
FIG. 3 is a partially exploded vertical cross-sectional view taken along lines B—B in FIG. 1.

FIG. 1 is an elevational view of the stent according to an embodiment of the present invention. FIG. 2 is an exploded transverse cross-sectional view taken along lines A—A in FIG. 1. FIG. 3 is a partially exploded vertical cross-sectional view taken along lines B—B in FIG. 1.

As shown in FIGS. 2 and 3, in the stent 1 of the present invention, a layer 3 of a biologically/physiologically active substance is formed on the surface of the wire member 2 constituting the stent main body to cover the stent main body, and a polymer layer 4 is formed on the biologically/physiologically active substance layer 3 to cover the biologically/physiologically active substance layer 3. However, the biologically/physiologically active substance layer 3 does not necessarily cover the entire surface of the wire members 2 constituting the stent main body, and the biologically/physiologically active substance layer 3 should cover at least a part of the wire members 2 constituting the stent main body. In other words, the embodiments are within the scope of the invention when only the surface of the wire member 2 corresponding to the outer surface of the stent main body, which is a cylindrical body, is covered with the biologically/physiologically active substance layer 3, or on the contrary, only the surface of the wire member 2 corresponding to the inner surface of the stent main body is covered with the biologically/physiologically active substance layer 3. The biologically/physiologically active substance layer 3, however, should always be covered with the polymer layer.

Next, the components constituting the stent 1 are described in further detail.

The stent main body is a cylindrical body having an opening on each end and extending in axial direction between the opposite ends. The side surface of the cylindrical body is formed with a large number of slots or holes which communicates the inner and the outer peripheral surfaces. The cylindrical body is radially expandable/compressible by the deformation or enlargement of the slots, and this radially expandable/compressible structure enables implantation of the stent in blood vessel or other vessel, or in bile duct or other body ducts in order to maintain the shape of the vessel or the duct.

In the embodiment shown in FIG. 1, the stent main body comprises resilient wires 2, and the stent main body is constituted from substantially diamond-shaped units 11 having slots in the inside. A plurality of substantially diamond-shaped units 11 are connected with each other so that the substantially diamond-shaped shapes are serially arranged in the direction of the minor axis of the diamond to constitute an annular unit 12. The annular unit 12 is connected with the adjacent annular unit by a wire resilient member 13, and as a consequence, a plurality of annular units 12 are serially arranged in the axial direction with a part thereof connected with each other. Since the stent main body (stent) 1 has the structure as described above, the stent main body comprises a cylindrical body having an opening on each end, and the cylindrical body extends in axial direction between the opposite ends. Since the stent main body (stent) 1 has the substantially diamond-shaped slots, the cylindrical body is radially expandable/compressible by the deformation of the slots.

It is to be noted that, in the present invention, the stent main body is not limited to the embodiment shown in the drawings, and included within the scope of the invention are any radially expandable cylindrical body having an opening on each end and extending in axial direction between the opposite ends, and having the structure with a large number of slots formed in the wall communicating the outer and the inner peripheral surfaces to enable the radial expansion/compression of the cylindrical body through the deformation of the slots.

Typical examples of the radially expandable/compressible stent main bodies include a stent main body as disclosed in JP 9-215753 A and JP 7-529 A wherein members formed by bending a resilient wire in coil shape are serially connected with each other to constitute a cylindrical body with the spaces between the resilient wires forming the slots; a stent main body as disclosed in JP 8-502428 A and JP 7-500272 A wherein members formed by bending a resilient wire in zigzag shape are serially connected with each other to constitute a cylindrical body with the spaces between the resilient wires forming the slots; a stent main body as disclosed in JP 2000-501328 A and JP 11-221288 A which has been produced by bending a resilient wire in the shape of serpentine flat ribbon, and the thus bent wire is helically wound around a mandrel to constitute a cylindrical body, with the spaces between the resilient wires forming the slots; a stent main body of mesh structure as disclosed in JP 10-503676 A wherein the slots are formed in meander pattern which are different from the stent main body of FIG. 1; and a stent main body as disclosed in JP 8-507243 A which has been produced by bending a plate member in coil shape to constitute a cylindrical stent main body wherein the spaces between the adjacent coil members corresponds to the slots. Other typical examples include cylindrical stent main bodies of different structures as disclosed in JP 4-68939 B wherein a resilient plate member is helically formed into a cylindrical body, with the spaces between the resilient plate members forming the slots; or wherein a resilient wire has been braided into a cylindrical body, with the spaces between the resilient wires forming the slots. In addition, the stent main body may be in the form of a coil of a plate spring, multiple helix, special pipe, and the like. There are also disclosed in FIGS. 2(a) and 2(b) of JP 4-68939 B a stent main body formed by helically winding a resilient plate member into a cylindrical body, and such cylindrical stent main body having expandable/compressible structure without providing any slot on the side wall may also be used as the stent main body of the present invention. All of the above publications and patent documents are herein incorporated by reference.

The means used for the expansion of the stent main body after leaving the stent in place is not particularly limited. The stent may be a self-expanding stent which expands in radially outward direction by its own restoring force, for example, by removing the strength which had maintained the stent main body folded in the smaller size. Alternatively, the stent may be a balloon-expandable stent wherein the stent main body is expanded in radially outward direction by an exterior force applied from the interior of the stent by an inflating balloon.

The stent main body may comprise a material such as a polymer material, a metal material, or a carbon fiber or ceramics, and the material used is not limited as long as the resulting stent has a certain degree of rigidity and elasticity. The stent, however, may preferably comprise a biocompatible material. Exemplary polymer materials used include polyethylene, polypropylene, and other polyolefins; polyethylene terephthalate and other polyesters; cellulose acetate, cellulose nitrate, and other cellulose polymers; polytetrafluoroethylene, tetrafluoroethylene-ethylene copolymer and other fluorine-containing polymers. Exemplary metal materials include stainless steel, tantalum, titanium, nickel-titanium alloy, tantalum-titanium alloy, nickel-aluminum alloy, inconel, gold, platinum, iridium, tungsten, and cobalt-based alloy. Of the stainless steel materials, SUS 316L is the most preferred in view of the corrosion resistance of highest degree.

The stent main body can be most favorably made when the material used is a material adequately selected from the materials as mentioned above according to the lesion where the stent is applied and the mean of its expansion. For example, when the stent main body is formed from a metal material, the stent can be reliably implanted in the lesion since a metal material is sufficient in strength. On the other hand, when the stent main body is formed from a polymer material, the stent will enjoy excellent deliverability owing to the high flexibility of the polymer material.

When the stent is a self-expandable stent, the stent is preferably made from a superelastic alloy such as titanium-nickel alloy since the stent should be capable of restoring its original shape. When the stent is a balloon-expandable stent, use of a material like, stainless steel is preferable since the stent after the expansion is unlikely to restore its original shape.

Also, when the stent main body is formed from a carbon fiber, the stent has high strength and is superior in flexibility and safety for implantation in the body.

An adequate size may be selected for the stent main body according to the lesion where it is applied. When it is applied, for example, in cardiac coronary artery, the stent main body may preferably have an outer diameter before the expansion of 1.0 to 3.0 mm, and a length of 5 to 50 mm.

In the case, the stent main body is constituted from a wire member as described above, a length of the wire member in its width direction is preferably 0.01 to 0.5 mm, more preferably 0.05 to 0.2 mm.

The way how the stent main body is produced is not limited to any particular method, and the production method may be adequately selected from those typically used in the art in the production of a stent.

In the stent of the present invention, the biologically/physiologically active substance layer is formed on the stent main body as described above to cover the surface of the wire member 2 constituting the stent main body. Also, when the stent main body is constituted from other constituent besides the wire member as exemplified above, for example, a sheet member, the biologically/physiologically active substance layer is formed on the stent main body to cover the surface of the constituent like a sheet member. The biologically/physiologically active substance layer 3 contains at least one biologically/physiologically active substance. The biologically/physiologically active substance incorporated in the biologically/physiologically active substance layer is not limited to any particular type as long as it has the effect of suppressing the restenosis of the lesion after implanting the stent of the present invention in the body duct. Exemplary biologically/physiologically active substances include a carcinostatic, an immunosuppressive, an antibiotic, an antirheumatic, an antithrombotic, an antihyperlipidemic, an ACE inhibitor, a calcium antagonist, an integrin inhibitor, an antiallergic, an antioxidant, a GPIIb/IIIa antagonist, retinoid, flavonoid, carotenoid, a lipid improving agent, a DNA synthesis inhibitor, a tyrosine kinase inhibitor, an antiplatelet, a vascular smooth muscle antiproliferative agent, an antiinflammatory agent, a biological material, an interferon, and a NO production accelerator.

Exemplary preferable carcinostatics include vincristine sulfate, vinblastine sulfate, vindesine sulfate, irinotecan hydrochloride, paclitaxel, docetaxel hydrate, methotrexate and cyclophosphamid.

Exemplary preferable immunosuppressives include sirolimus, tacrolimus hydrate, azathioprine, cyclosporin, mycophenolatemofetil, gusperimus hydrochloride, and mizoribine.

Exemplary preferable antibiotics include mitomycin C, doxorubicin hydrochloride, actinomycin D, daunorubicin hydrochloride, idarubicin hydrochloride, pirarubicin hydrochloride, aclarubicin hydrochloride, epirubicin hydrochloride, peplomycin sulfate, and zinostatin stimalamer.

Exemplary preferable antirheumatics include sodium aurothiomalate, penicillamine, and lobenzarit disodium.

Exemplary preferable antithrombotics include heparin, ticlopidine hydrochloride, and hirudin.

Exemplary preferable antihyperlipidemic include HMG-CoA reductase inhibitors and probucol. Exemplary preferable HMG-CoA reductase inhibitors include serivastatin sodium, atolvastatin, nisvastatin, pitavastatin, fluvastatin sodium, simvastatin, lovastatin, and pravastatin potassium.

Exemplary preferable ACE inhibitors include quinapril hydrochloride, perindopril erbumine, trandolapril, cilazapril, temocapril hydrochloride, delapril hydrochloride, enalapril maleate, lisinopril, and captopril.

Exemplary preferable calcium antagonists include nifedipine, nilvadipine, diltiazem hydrochloride, benidipine hydrochloride, and nisoldipine.

Exemplary preferable antiallergics include tranilast.

Exemplary preferable retinoids include all-trans retinoic acid.

Exemplary preferable antioxidants include catechines, anthocyanine, proanthocyanidin, lycopene, and β-carotene. Of the catechines, the most preferred is epigallocatechin gallate.

Exemplary preferable tyrosine kinase inhibitors include genistein, tyrphostin, and apstatin.

Exemplary preferable antiinflammatories include dexamethasone, prednisolone, and other steroids, and aspirin.

Exemplary preferable biological materials include EGF (epidermal growth factor), VEGF (vascular endothelial growth factor), HGF (hepatocyte growth factor), PDGF (platelet derived growth factor), and BFGF (basic fibroblast growth factor).

The biologically/physiologically active substance layer may contain only one of the biologically/physiologically active substance as mentioned above, or alternatively, two or more different biologically/physiologically active substances of the combination adequately selected from the biologically/physiologically active substances as mentioned above.

The method employed to form the biologically/physiologically active substance layer 3 on the surface of the wire member 2 constituting the stent main body is not limited to any particular method as long as the biologically/physiologically active substance layer 3 can be uniformly deposited on the surface of the wire member 2 constituting the stent main body. For example, the layer 3 can be deposited by heating and melting the biologically/physiologically active substance, and coating the molten substance on the surface of the wire member 2 constituting the stent main body; or by heating and melting the biologically/physiologically active substance, and dipping the stent main body in the molten biologically/physiologically active substance followed by cooling and solidification of the biologically/physiologically active substance to thereby form the biologically/physiologically active substance layer 3. Alternatively, the layer 3 may be formed by dissolving the biologically/physiologically active substance in an adequate solvent to thereby form a solution and dipping the stent main body in the solution, and after recovering the stent main body from the solution, removing the solvent by evaporation or other method to thereby form a coating on the wire member 2 constituting the stent main body; or by coating such solution on the wire member 2 constituting the stent main body by spraying such solution with a spray device or other means, or by accomplishing the coating by other means, and removing the solvent by evaporation or other method to thereby form a coating on the wire member 2 constituting the stent main body.

It is to be noted that, when the biologically/physiologically active substance is insufficient in adhesion to the wire member 2 constituting the stent main body, and the biologically/physiologically active substance used alone is unlikely to be able to form a layer on the surface of the wire member 2 constituting the stent main body, the solution is preferably supplemented with an additional component which imparts tackiness to the biologically/physiologically active substance. To be more specific, when the biologically/physiologically active substance is a water soluble, low molecular weight substance having a molecular weight of up to 1000, the solution is preferably supplemented with the additional component, for example, a saccharide such as a monosaccharide, a disaccharide, an oligosaccharide, or the like, or a water-soluble vitamin. When the biologically/physiologically active substance is a water soluble, high molecular weight substance having a molecular weight of over 1000, the solution is preferably supplemented with the additional component which is dextran, hydroxy ethyl cellulose, or the like. When the biologically/physiologically active substance is a fat soluble substance, the solution is preferably supplemented with the additional component which is a low molecular weight higher fatty acid having a molecular weight of up to 1000 such as a fish oil, a vegetable oil, a fat-soluble vitamine such as vitamine A or vitamine E.

It is to be noted that, when there is an adequate solvent for dissolving the biologically/physiologically active substance, and the biologically/physiologically active substance used alone is capable of forming a layer on the surface of the wire member 2 constituting the stent main body, the layer 3 can be most conveniently and favorably formed by preparing a solution of the biologically/physiologically active substance alone in the solvent, and dipping the stent main body in the solution followed by drying, or alternatively, by spraying such solution on the wire member 2 constituting the stent main body followed by drying.

The biologically/physiologically active substance layer 3 may have a quantity adequately determined depending on the shape and size of the stent. To be more specific, the quantity may be adequately determined so that the effect of releasing the biologically/physiologically active substance is sufficiently achieved without detracting from the performance of the stent main body such as deliverability of the stent to the lesion and reduced irritation for the blood vessel wall. The quantity of the biologically/physiologically active substance layer 3 is preferably in the range of 0.1 to 3 mg(/cm$^2$).

In the stent of the present invention, the polymer layer 4 is formed on the biologically/physiologically active substance layer 3 as described above to cover the layer 3. The polymer layer 4 comprises a vapor or water-permeable polymer having a water-swellable substance 5 dispersed in the water-permeable polymer. The water-swellable substance 5 is swollen when it absorbs the vapor or the water.

The polymer constituting the polymer layer 4 is vapor or water permeable, and cracks are formed in this polymer when the water-swellable substance 5 dispersed therein is swollen by absorbing the vapor or the water. To be more specific, this polymer satisfies the following conditions:

water content: less than 10% (35° C.)

coefficient of vapor permeability: more than $10^{-7}$ [cm$^3$ (STP) (cm·s·cmHg)$^{-1}$]

tensile strength: up to 30 MPa tear strength: up to 100 kg/cm

The polymer constituting the polymer layer is not particularly limited as long as it satisfies the conditions as described above. The polymer, however, is used for a stent which is implanted in the body, and therefore, should be biologically safe and less irritant to the tissue where it is implanted. Exemplary such polymers include silicone polymers such as silicone elastomers, cellulose polymers, polyurethanes, polyesters, vinyl polymers such as ethylene vinyl acetate copolymers (EVA), acrylic polymers, and thermoplastic elastomers, which satisfy the conditions as described above. Of these polymers, the most preferred are silicone elastomers and EVA.

The silicone elastomer generally includes elastomer compositions which mainly comprises a dialkyl polysiloxane, which may be a straight chain or a branched dialkyl polysiloxane, and also included are those containing vinyl group, those wherein the alkyl group is partly substituted with hydrogen atom, and those which has been amino or halogen modified. However, 90% or more of the alkyl group constituting the dialkyl polysiloxane is methyl group. The silicone elastomer may preferably have a viscosity before the curing of more than 500 cps, and a hardness after the curing of 20 to 80 durometer hardness, shore A. It is to be noted that use of a two part silicone elastomer is preferable in view of the working convenience in the formation of the polymer layer. The silicone elastomer used may be a commercially available product as long as the conditions as described above are satisfied. Exemplary preferable commercial available product include the SILASTIC (manufactured by DOW CORNING CORPORATION), the SILICONE Elastmer (MED-4211) (manufactured by Nusil Technology).

The EVA used may preferably contain the ethylene and the vinyl acetate at a weight ratio of 60:40 to 95:5, and the EVA may preferably have a melt flow rate (MFR) 1 to 60 g/10 min.

The most preferred is the silicone elastomer as described above.

The polymer as described above may also contain a plastic agent, a filler, or the like at a content that does not adversely affect the object of the present invention.

The method employed to cover the surface of the biologically/physiologically active substance layer 3 with the polymer layer 4, and the method employed to disperse the water-swellable substance 5 in the polymer layer 4 is not particularly limited as long as the biologically/physiologically active substance layer 3 is fully covered with the polymer layer, and the water-swellable substance 5 is fully dispersed in the polymer layer 4. Exemplary methods include a method wherein the polymer and the water-swellable substance 5 are dissolved in a solvent to prepare a solution, and the stent main body preliminarily covered with the biologically/physiologically active substance layer 3 is dipped in the solution followed by drying, and the method wherein the solution is sprayed on the wire member 2 constituting the stent main body preliminarily covered with the biologically/physiologically active substance layer 3 by using a spray followed by drying.

The thickness of the polymer layer 4 is determined as in the case of the biologically/physiologically active substance layer 3 so as not to impair the performance of the stent main body such as deliverability to the lesion and reduced irritation to the vascular wall. The polymer layer 4 is preferably formed to a thickness of 1 to 75 μm, more preferably to a thickness of 10 to 50 μm, and most preferably to a thickness of 20 to 30 μm. When the polymer layer 4 has a thickness of less than 1 μm, the particle size of the water-swellable substance 5 dispersed in the polymer layer exceeds the thickness of the polymer layer and the polymer layer will not be able to perform the function of fully covering the biologically/physiologically active substance layer 3. On the other hand, when the thickness of the polymer layer 4 is in excess of 75 μm, outer diameter of the stent 1 itself will be so large that the stent may detract from the deliverability, and in particular the deliverability to the lesion.

The water-swellable substance 5 is not particularly limited as long as the substance is swollen by absorbing the vapor or the water and the substance is safe in medical point of view even if it dissolved into blood or other body fluid, and it may be either a high molecular weight substance or a low molecular weight substance. However, use of fine particles of a high molecular weight, superabsorbent substance such as a metal chelate of polyacrylate for the water-swellable substance is associated with the risk of accumulation of the substance which has dissolved into the body fluid, and use of a low molecular weight substance having a molecular weight of up to 1000 which is free from such risk is preferable. To be more specific, the low molecular weight substance used is preferably a low molecular weight salt (the term "low molecular weight salt" is an ionic compound derived by neutralization between the acid and the base) having a molecular weight of up to 1000 which is easily dispersed in the polymer layer 4. More preferably, the low molecular weight salt is a salt which is present in a living body in view of the low irritation to the body. Exemplary such low molecular weight salts include sodium chloride, sodium carbonate, sodium hydrogen carbonate, sodium dihydrogen phosphate, sodium monohydrogen phosphate, sodium lactate, sodium acetate, and sodium salt of an amino acid, potassium chloride, potassium dihydrogen phosphate, potassium monohydrogen phosphate, potassium lactate, potassium acetate and potassium salt of an amino acid, magnesium sulfate, magnesium chloride and magnesium salt of an amino acid. In consideration of the swelling and osmotic pressure in the polymer layer 4 and dissolution in the body duct, use of sodium chloride is most preferable since it is a low molecular weight substance which is present in the body at a high degree.

The water-swellable substance 5 is preferably used at a concentration of 0.01 to 10% by mass, more preferably at 0.05 to 5% by mass, and most preferably at 0.1 to 2.5% by mass in relation to the mass of the polymer constituting the polymer layer 4. When the concentration of the water-swellable substance 5 is in excess of 10% by mass in relation to the mass of the polymer constituting the polymer layer 4, there is a risk that excessive cracks are generated in the polymer layer 4 upon swelling of the water-swellable substance by the water or vapor absorption to result in the difficulty of controlling the release speed of the biologically/physiologically active substance. On the other hand, when the concentration of a low molecular weight salt is less than 0.01% by mass, there is a risk that the cracks generated in the polymer layer 4 are insufficient with the biologically/physiologically active substance failing to be released outside the sustained release coating.

The particle size of the water-swellable substance 5 at the addition to the polymer layer 4 is not particularly limited as long as the size allows smoothness of the outer surface of the polymer layer 4 and generation of the cracks in the polymer layer 4. The particle size, however, is preferably in the range of 1 to 50 μm, more preferably 3 to 30 μm, and most preferably 5 to 30 μm in view of the thickness of the polymer layer 4.

Any desired combination of the polymer to constitute the polymer layer 4 and the water-swellable substance 5 may be chosen as long as the cracks are generated in the polymer upon swelling of the water-swellable substance by the water or vapor absorption. The preferable combination, however, is use of sodium chloride having a particle size of 5 to 30 μm as a water-swellable substance dispersed in the silicone elastomer as described above at a concentration of 0.1 to 2.5% by mass.

Next, mechanism of the release of the biologically/physiologically active substance from the sustained release coating is described.

Figure 4:
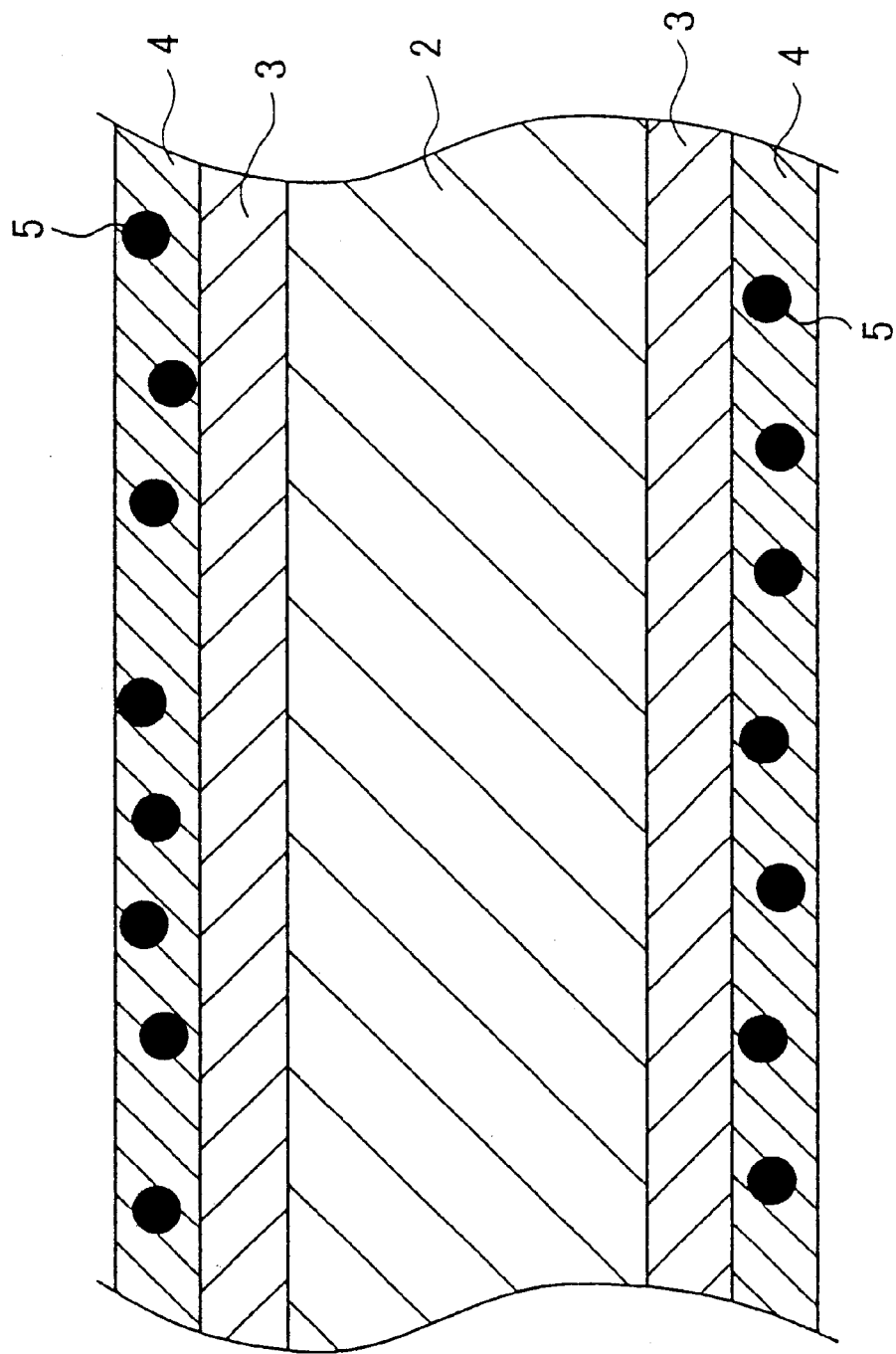
FIG. 4 is a partially exploded vertical cross-sectional view of the stent of FIG. 3 when the water-swellable substance has been swollen.

Once the stent 1 is implanted in the lesion, the vapor or the water that has been present in the body duct starts to intrude into the polymer layer 4. The term "vapor" used herein is the one formed by vaporization of the blood or other body fluid in the body duct. The vapor or the water that has intruded into the polymer layer 4 then becomes entrapped in the water-swellable substance 5 in the polymer layer 4, and the water-swellable substance 5 that entrapped the water or the vapor is swollen by absorbing the water or the vapor. As a consequence, volume of the water-swellable substance 5 increases in the polymer layer 4 as shown in FIG. 4.

Figure 5:
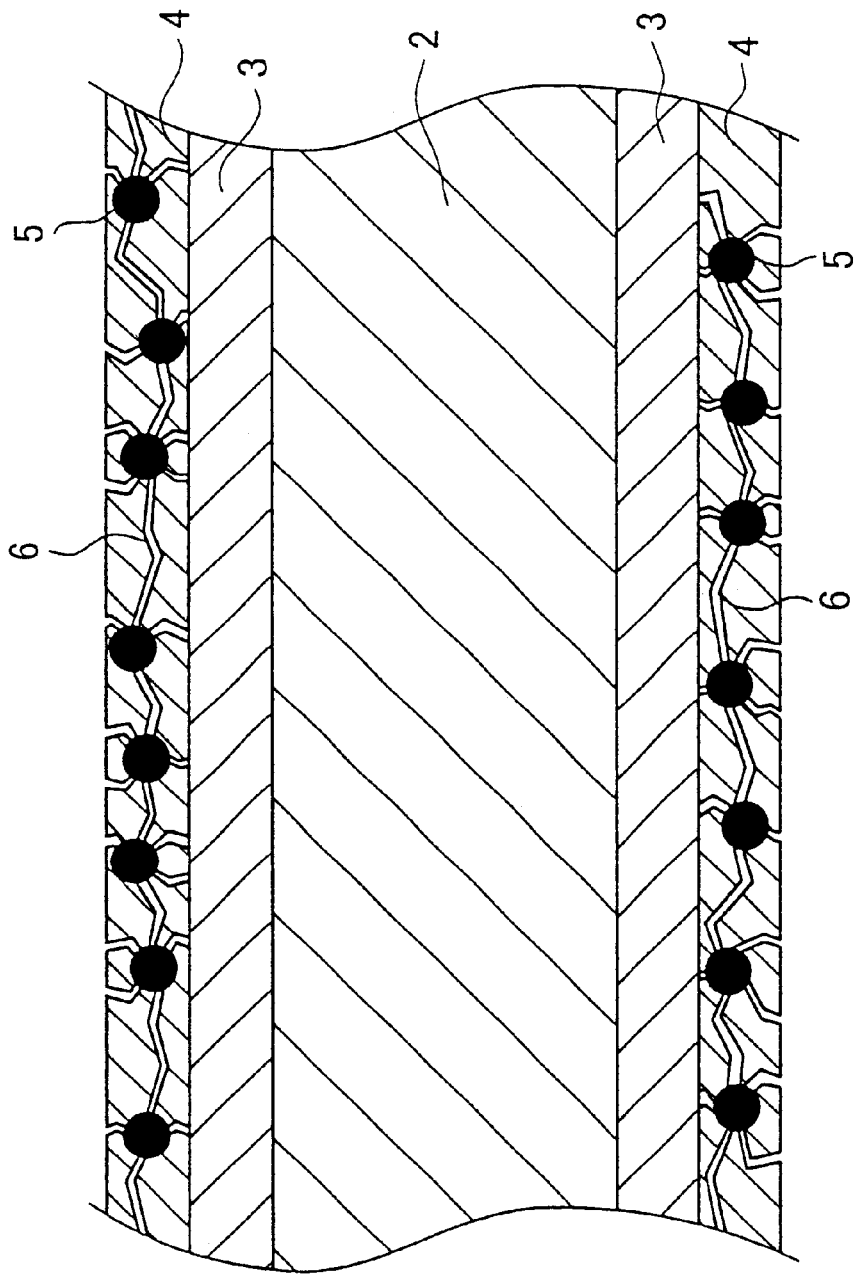
FIG. 5 is a partially exploded vertical cross-sectional view of the stent of FIG. 3 when cracks have generated in the polymer layer.

The polymer constituting the polymer layer 4 then receives continuous force from the swelling water-swellable substance 5, and breakage occurs at various parts of the polymer resulting in the cracks 6 of the polymer layer 4 as shown in FIG. 5. The cracks 6 occur at a number of sites in the polymer layer 4 as shown in FIG. 5 as the consequence of the continuously applied force by the swelling of the water-swellable substance 5, and a network of cracks is formed by the linking of the cracks 6. This network finally penetrates the polymer layer 4, and a passage is formed in the polymer layer 4 to enable moving of the biologically/physiologically active substance.

Through this passage, the body fluid and other fluids in the body duct becomes in contact with the biologically/physiologically active substance layer 3, and the biologically/physiologically active substance then dissolves into the fluid. This mechanism is not affected by the properties of the biologically/physiologically active substance, namely, whether the biologically/physiologically active substance is water- or fat-soluble since most of the body fluids including the blood contain fatty components in addition to the water which constitutes most of the fluid.

It is believed that the thus dissolved biologically/physiologically active substance passes through the passage formed in the polymer layer 4 to be released to the exterior of the sustained release coating. When the water-swellable substance 5 is sodium chloride or other low molecular weight salt, the salt will dissolve into the body fluid or other liquid to become released through the passage to the exterior of the sustained release coating. The space where the water-swellable substance 5 had occupied then becomes empty, and this space will form a part of the passage as described above.

As described above, in the stent 1 of the present invention, there are no passages communicating the biologically/physiologically active substance layer 3, and the surface of the stent 1 (the surface of the polymer layer 4) before the insertion of the stent in the body and contact of the stent with the blood or other body fluid. The passage is formed in the polymer layer 4 only after the implantation of the stent in the lesion of the body duct and contact of the stent with the body fluid. As a consequence, the biologically/physiologically active substance is prevented from being rapidly released in a short period (within several days after the implantation of the stent 1 in the lesion), and instead, the biologically/physiologically active substance undergoes a sustained, gradual release for a prolonged period (in several weeks to several months after the implantation of the stent 1 in the lesion). The release of the biologically/physiologically active substance from the stent 1 is also prevented before the insertion in the body.

Furthermore, in the stent 1 of the present invention, the polymer layer 4 and the biologically/physiologically active substance layer 3 are separately provided as different layers, and this stent is free from the problem of the biologically/physiologically active substance being decomposed or degraded by the action of the polymer. As a consequence, the biologically/physiologically active substance can be loaded on the wire member 2 constituting the stent main body in a stable manner until it is released from the stent 1. Also, no limitation is set on the combination of the polymer and the biologically/physiologically active substance.

EXAMPLES

Next, the present invention is described in further detail by referring to the Examples which by no means limit the scope of the present invention.

Example 1

A cylindrical stent main body (material, SUS 316L) having substantially diamond-shaped slots as shown in FIG. 1 was used. This stent main body had an outer diameter of 1.8 mm and a length of 30 mm. The outer surface of the wire member (width, 0.2 mm) was sprayed with a solution of vincristine sulfate, (hereinafter referred to as "VS") in dichloromethane (VS concentration, 10% by weight). VS is a carcinostatic, and this substance was used as a biologically/physiologically active substance. A hand spray (HP-C, manufactured by IWATA) was used in the spraying. It was then confirmed that about 2 mg of VS was coated on the outer surface of the wire member constituting the stent main body. The solvent, dichloromethane was completely volatilized to form a layer of the biologically/physiologically active substance (VS layer) on the surface of the stent main body. Next, a two part silicone elastomer (MED-4211, manufactured by NUSIL) prepared by adding 1 g of a curing agent to 10 g of a base compound was dispersed in 89 g of hexane to prepare a silicone elastomer solution (silicone elastomer concentration, 10% by weight), and sodium chloride fine powder (particle size, up to 30 μm) was added to this silicone elastomer solution so that the concentration of the sodium chloride in relation to the total weight of the base compound and the curing agent of the silicone elastomer and the sodium chloride was 2.5% by weight. This solution was then sprayed by using a hand spray (HP-C, manufactured by IWATA).

After confirming that the polymer layer had fully covered the biologically/physiologically active substance layer, the stent was heated in an oven at 60° C. for 24 hours to thereby form the polymer layer. The polymer layer after the thermosetting had a thickness at an average of 50 μm. This stent was evaluated for the amount of the biologically/physiologically active substance (VS) released.

The measurement was conducted by dipping the resulting stent in 50 ml of phosphate buffer solution (pH 7.0), and placing the solution in a thermostat bath at 37° C. Sample of the phosphate buffer solution was collected at a predetermined time interval to measure the amount of the VS released.

The amount of the VS in the collected phosphate buffer solution, namely, the amount of the VS released from the stent was determined by measuring absorbance at a wavelength of 298 nm by using a spectrophotometer (UV-2400PC, manufactured by Shimadzu), and calculating the amount by using a calibration curve which had been prepared in advance. The results are shown in Table 1. It is to be noted that the amount of the VS released shown in Table 1 is indicated by the proportion (%) in the amount of the VS that had been coated on the wire member constituting the stent main body.

As evident from Table 1, it was confirmed that the amount of the VS released increased with the increase in time (day), and that the VS was slowly released for about 4 weeks with no rapid release in short period (initial burst).

Figure 6:
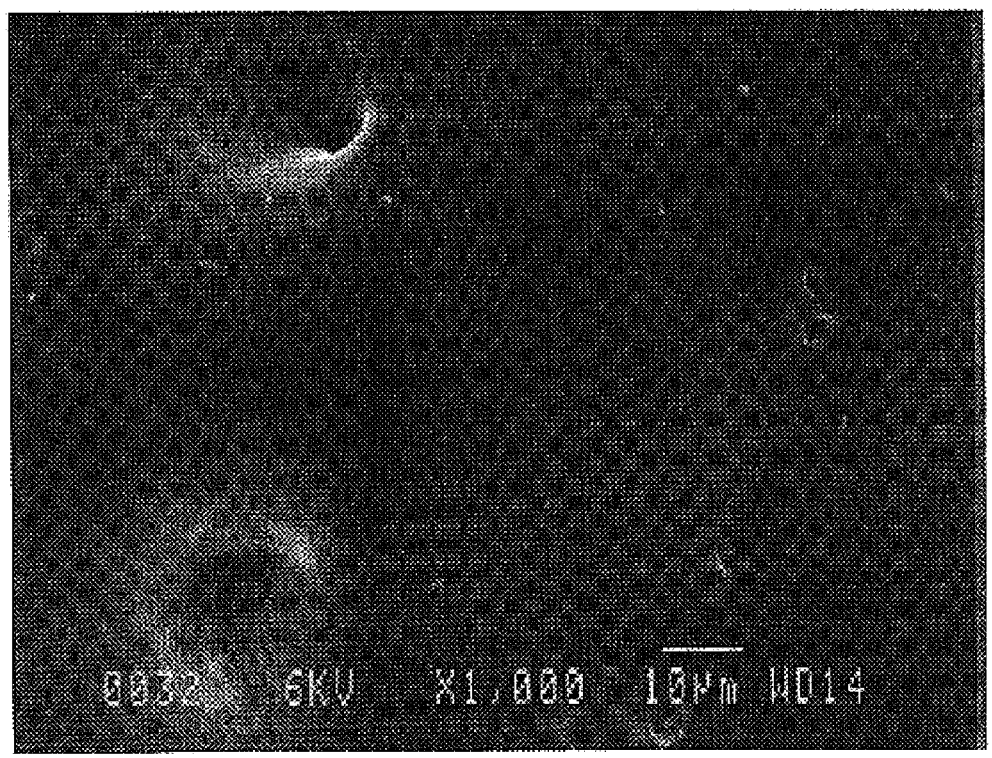
FIG. 6 is an electron micrograph (magnification, 1000×) of the polymer layer surface of the stent of Example 1 after immersing the stent in phosphate buffer solution.
Figure 7:
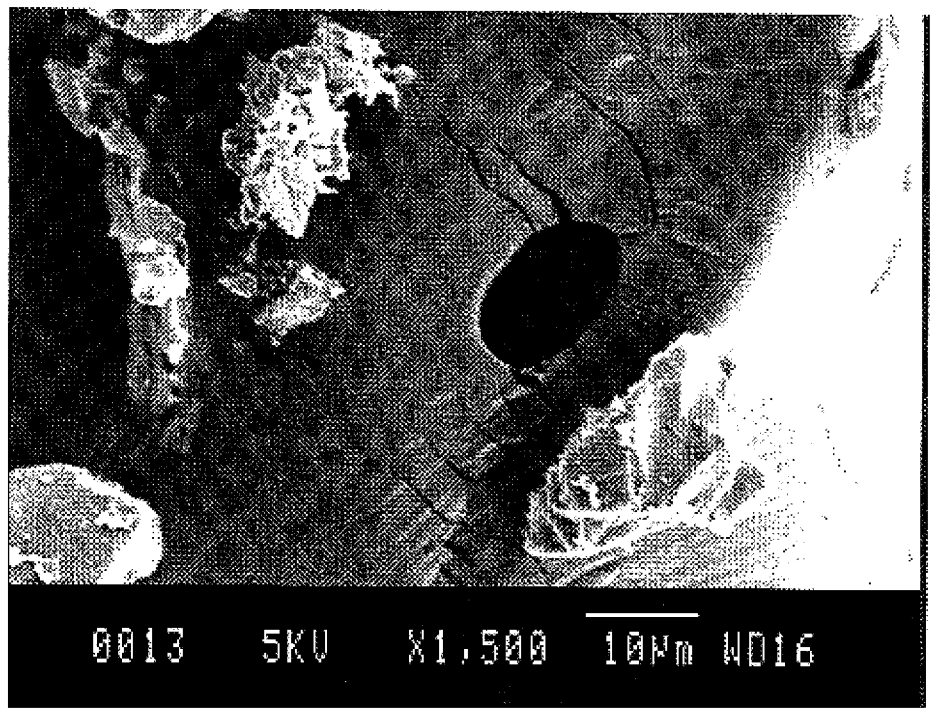
FIG. 7 is an electron micrograph (magnification, 1500×) of the cross section of the polymer layer of the stent of Example 1 after immersing in phosphate buffer solution.

For the stent of the Example 1, electron micrographs of the surface of the polymer layer after the dipping in the phosphate buffer solution for 24 hours were taken. FIG. 6 is a frontal electron micrograph (1000×) of the polymer layer after the dipping in the phosphate buffer solution, and formation of holes in the polymer layer can be confirmed in this electron micrograph. FIG. 7 is a cross sectional electron micrograph (1500×) of the polymer layer after the dipping in the phosphate buffer solution, and generation of cracks in the polymer layer is indicated in this electron micrograph. The holes and cracks found in the polymer layer after the dipping proved generation of the cracks in the polymer layer and formation of the passages penetrating the polymer layer which constitute the release mechanism of the biologically/physiologically active substance from the sustained release coating by the swelling of the water-swellable substance.

Example 2

The outer surface of the wire member constituting the stent main body which is the same as Example 1 was sprayed with a solution of VS in dichloromethane (VS concentration, 10% by weight) by using a hand spray. It was then confirmed that about 2 mg of VS was coated on the outer surface of the wire member constituting the stent main body. The solvent, dichloromethane was completely volatilized to form a layer of the biologically/physiologically active substance on the surface of the stent main body. Next, MED-4211 prepared by adding 1 g of a curing agent to 10 g of a base compound was dispersed in 89 g of hexane to prepare a solution (silicone elastomer concentration, 10% by weight), and sodium chloride fine powder (particle size, up to 30 μm) was added to this solution so that the concentration of the sodium chloride in relation to the total weight of the base compound and the curing agent of the silicone elastomer and the sodium chloride was 1.0% by weight. The resulting solution was then sprayed by using a hand spray. After confirming that the polymer layer had fully covered the biologically/physiologically active substance layer, the stent was heated in an oven at 60° C. for 24 hours to thereby form the polymer layer. The polymer layer after the thermosetting had a thickness at an average of 50 μm. This stent was evaluated for the amount of the biologically/physiologically active substance (VS) released. The measurement was conducted as in the case of Example 1. The results are shown in Table 1. As in the case of Example 1, the amount of the VS released is indicated by the proportion (%) in the amount of the VS that had been coated on the wire member constituting the stent main body.

As evident from Table 1, it was confirmed that the amount of the VS released increased with the increase in time (day), and that the VS was slowly released for about 4 weeks with no rapid release in short period (initial burst).

Comparative Example 1

The outer surface of the wire member constituting the stent main body which is the same as Example 1 was sprayed with a solution of VS in dichloromethane (VS concentration, 10% by weight) by using a hand spray. It was then confirmed that about 2 mg of VS was coated on the outer surface of the wire member constituting the stent main body. The solvent, dichloromethane was completely volatilized to form a layer of the biologically/physiologically active substance on the surface of the stent main body. Next, MED-4211 prepared by adding 1 g of a curing agent to 10 g of a base compound was dispersed in 89 g of hexane to prepare a solution (silicone elastomer concentration, 10% by weight), and this solution was sprayed by using a hand spray. After confirming that the polymer layer had fully covered the biologically/physiologically active substance layer, the stent was heated in an oven at 60° C. for 24 hours to thereby form the polymer layer. The polymer layer after the thermosetting had a thickness at an average of 50 $\mu$m. This stent was evaluated for the amount of the biologically/physiologically active substance (VS) released. The measurement was conducted as in the case of Example 1. The results are shown in Table 1. As in the case of Example 1, the amount of the VS released is indicated by the proportion (%) in the amount of the VS that had been coated on the wire member constituting the stent main body.

As evident from Table 1, it was confirmed that the VS is barely released in the system wherein the polymer layer does not contain sodium chloride.

Figure 8:
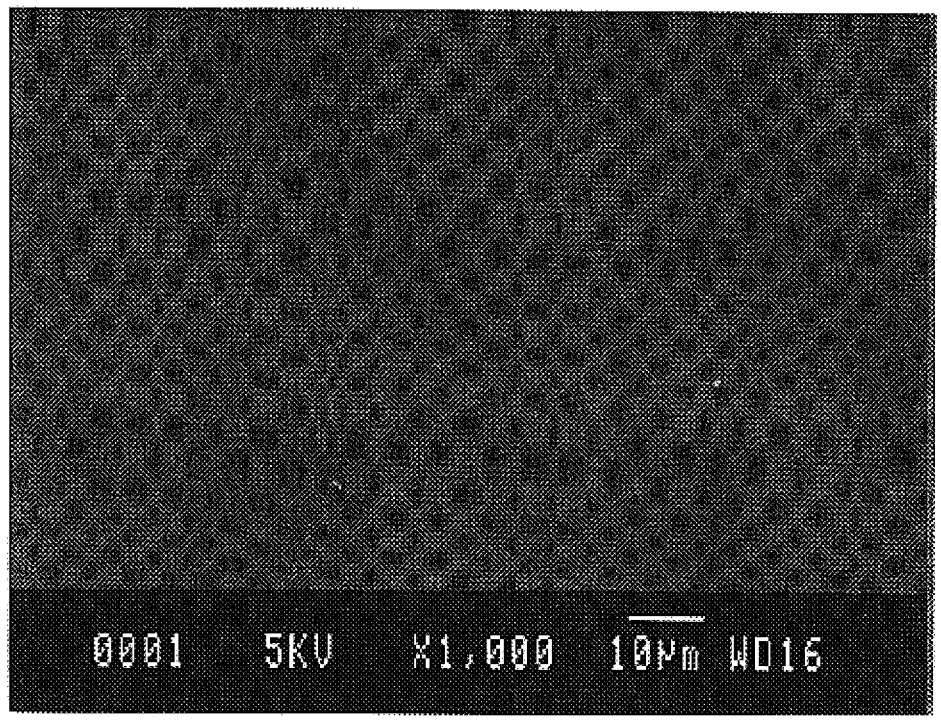
FIG. 8 is an electron micrograph (magnification, 1000×) of the polymer layer surface of the stent of Comparative Example 1 after immersing the stent in phosphate buffer solution.
Figure 9:
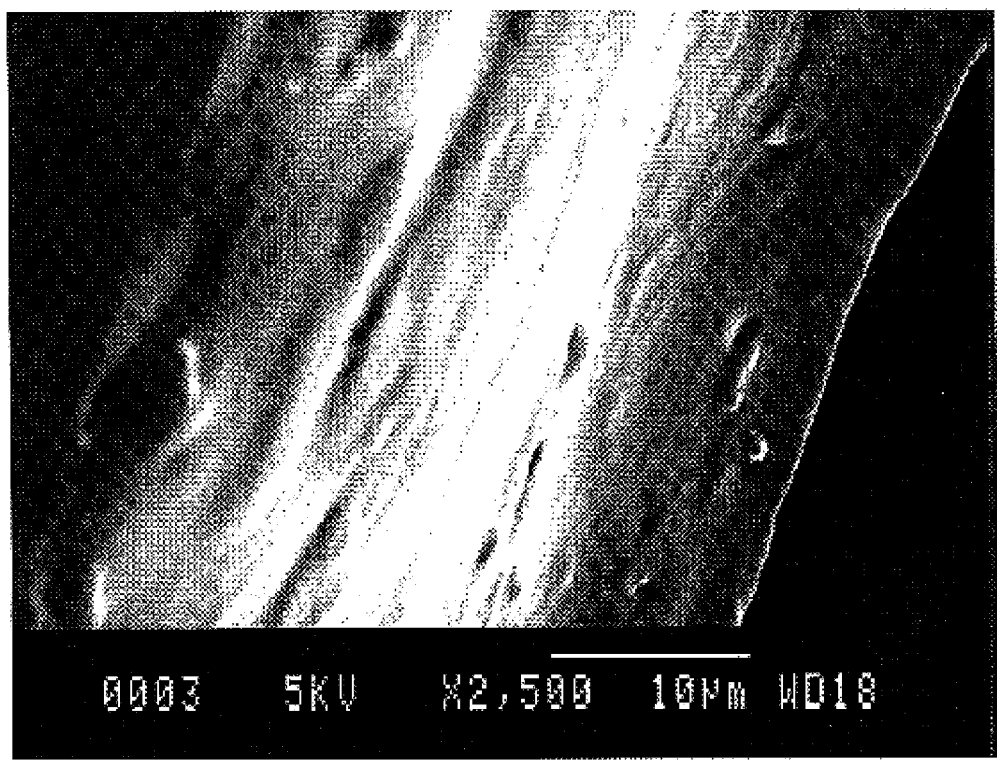
FIG. 9 is an electron micrograph (magnification, 2500×) of the cross section of the polymer layer of the stent of Comparative Example 1 after immersing in phosphate buffer solution.

For the stent of the Comparative Example 1, electron micrographs (1000×) of the polymer layer after the dipping in the phosphate buffer solution for 24 hours were taken. FIG. 8 is a frontal electron micrograph of the surface of the polymer layer after the dipping in the phosphate buffer solution, and absence of holes in the polymer layer can be confirmed by comparing the photomicrograph with FIG. 6. FIG. 9 is a cross sectional electron micrograph (2500×) of the polymer layer after the dipping in the phosphate buffer solution, and absence of the holes and the cracks can be confirmed by comparing the photomicrograph with FIG. 7.

Example 3

The outer surface of the wire member constituting the stent main body which is the same as Example 1 was sprayed with a solution of epigallocatechin gallate (hereinafter referred to as "EGCG", which is a polyphenol and an antioxidant) in ethanol (EGCG concentration, 10% by weight) by using a hand spray. It was then confirmed that about 2 mg of EGCG was coated on the outer surface of the wire member constituting the stent main body. The solvent, ethanol was completely volatilized to form a layer of the biologically/physiologically active substance on the surface of the stent main body. Next, MED-4211 prepared by adding 1 g of a curing agent to 10 g of a base compound was dispersed in 89 g of hexane to prepare a solution (silicone elastomer concentration, 10% by weight), and sodium chloride fine powder (particle size, up to 30 $\mu$m) was added to this solution so that the concentration of the sodium chloride in relation to the total weight of the base compound and the curing agent of the silicone elastomer and the sodium chloride was 2.5% by weight. The resulting solution was then sprayed by using a hand spray. After confirming that the polymer layer had fully covered the biologically/physiologically active substance layer, the stent was heated in an oven at 60° C. for 24 hours to thereby form the polymer layer. The polymer layer after the thermosetting had a thickness at an average of 50 $\mu$m. This stent was evaluated for the amount of the biologically/physiologically active substance (EGCG) released.

The measurement was conducted by dipping the resulting stent in 50 ml of phosphate buffer solution (pH 7.0), and placing the solution in a thermostat bath at 37° C. Sample of the phosphate buffer solution was collected at a predetermined time interval to measure the amount of the EGCG released.

The amount of the EGCG in the collected phosphate buffer solution, namely, the amount of the EGCG released from the stent was determined by measuring absorbance at a wavelength of 275 nm by using a spectrophotometer, and calculating the amount by using a calibration curve which had been prepared in advance. The results are shown in Table 2. It is to be noted that the amount of the EGCG released shown in Table 1 is indicated by the proportion (%) in the amount of the EGCG that had been coated on the wire member constituting the stent main body.

As evident from Table 2, it was confirmed that the amount of the EGCG released increased with the increase in time (day), and that the EGCG was slowly released for about 4 weeks with no rapid release in short period (initial burst).

Comparative Example 2

The outer surface of the wire member constituting the stent main body which is the same as Example 1 was sprayed with a solution of EGCG in ethanol (EGCG concentration, 10% by weight) by using a hand spray. It was then confirmed that about 2 mg of EGCG was coated on the outer surface of the wire member constituting the stent main body. The solvent, ethanol was completely volatilized to form a layer of the biologically/physiologically active substance on the surface of the stent main body. Next, MED-4211 prepared by adding 1 g of a curing agent to 10 g of a base compound was dispersed in 89 g of hexane to prepare a solution (silicone elastomer concentration, 10% by weight), and this solution was sprayed by using a hand spray. After confirming that the polymer layer had fully covered the biologically/physiologically active substance layer, the stent was heated in an oven at 60° C. for 24 hours to thereby form the polymer layer. The polymer layer after the thermosetting had a thickness at an average of 50 $\mu$m. This stent was evaluated for the amount of the biologically/physiologically active substance (EGCG) released. The measurement was conducted as in the case of Example 3. The results are shown in Table 2. As in the case of Example 3, the amount of the EGCG released is indicated by the proportion (%) in the amount of the EGCG that had been the wire member constituting the stent main body.

As evident from Table 2, it was confirmed that the EGCG is barely released in the system wherein the polymer layer does not contain sodium chloride.

TABLE 1

Amount of VS released

| Time (day) | Example 1 | Example 2 | Comparative Example 1 |
|---|---|---|---|
| 1 | 3.0 | | |
| 3 | | | 5.0 |
| 4 | | 5.9 | |
| 5 | 17.8 | | |
| 6 | | | 4.6 |
| 11 | 48.0 | 32.8 | 4.6 |
| 14 | 57.7 | | |
| 16 | | 38.9 | |
| 18 | | | 5.2 |
| 20 | | 43.3 | |
| 24 | | 48.2 | |
| 28 | 78.3 | | |
| 31 | | 52.5 | |

The amount of the VS released shown in Table is indicated by the proportion (%) in the amount of the VS that had been coated on the wire member constituting the stent main body.

TABLE 2

Amount of EGCG released

| Time (day) | Example 3 | Comparative Example 2 |
|---|---|---|
| 1 | | |
| 3 | 2.5 | 1.5 |
| 8 | 6.1 | |
| 13 | 28.7 | 1.5 |
| 17 | 47.0 | |
| 21 | 75.4 | 1.8 |
| 28 | 78.7 | |

The amount of the EGCG released shown in Table is indicated by the proportion (%) in the amount of the EGCG that had been coated on the wire member constituting the stent main body.

MERIT OF THE INVENTION

As described above, the present invention is directed to a stent to be implanted in a body duct, and this stent comprises the stent main body and the sustained release coating formed on the surface of the stent main body. The sustained release coating comprises the biologically/physiologically active substance layer which is formed on the surface of the wire members constituting the stent main body and contains at least one biologically/physiologically active substance, and the polymer layer formed on the biologically/physiologically active substance layer to cover the biologically/physiologically active substance layer. The polymer layer comprises the vapor or water-permeable polymer, and the water-swellable substance dispersed in the polymer and swollen by absorption of the vapor or water. Since cracks are formed in the polymer layer when the water-swellable substance is swollen by the vapor or water, and the biologically/physiologically active substance layer is released to the exterior of the sustained release coating through the polymer layer, the biologically/physiologically active substance can be stably loaded on the stent main body without undergoing decomposition or degradation. In addition, once the stent is implanted in the lesion, the biologically/physiologically active substance undergoes a sustained release, namely gradual release for a prolong period without being rapidly released in a short period.

When the stent main body is formed from a metal material, reliable implantation of the stent at the lesion is enabled due to the excellent strength of the metal material.

When the stent main body is formed from a polymer material, the stent enjoys the merit of excellent deliverability to the lesion since the polymer material is highly flexible.

When the biologically/physiologically active substance layer is solely formed from the biologically/physiologically active substance, the biologically/physiologically active substance layer can be formed by a simple procedure.

When the biologically/physiologically active substance used alone is insufficient in its adhesion to the surface of the wire members constituting the stent main body, an additional component which imparts tackiness to the biologically/physiologically active substance layer may be mixed with the biologically/physiologically active substance to thereby improve the adhesion to the wire members constituting the stent main body.

The stent can suppress the restenosis of the lesion where the stent has been implanted when the biologically/physiologically active substance is at least one member selected from a carcinostatic, an immunosuppressive, an antibiotic, an antirheumatic, an antithrombotic, an antihyperlipidemic, an ACE inhibitor, a calcium antagonist, an integrin inhibitor, an antiallergic, an antioxidant, a GPIIb/IIIa antagonist, retinoid, flavonoid, carotenoid, a lipid improving agent, a DNA synthesis inhibitor, a tyrosine kinase inhibitor, an antiplatelet, a vascular smooth muscle antiproliferative agent, an antiinflammatory agent, a biological material, an interferon, and a NO production accelerator.

The biological safety of the stent will be particularly high when the polymer layer is formed from a polymer selected from a silicone polymer, a cellulose polymer, a polyurethane, a polyester, a vinyl polymer, an acrylic polymer, and a thermoplastic elastomer.

The dispersion of the water-swellable substance in the polymer layer will be facilitated when the water-swellable substance is a low molecular weight salt having a molecular weight of up to 1000.

When a low molecular weight salt is the salt which is found in a body, the stent produced is highly safe due to the low irritation of the low molecular weight salt.

When the low molecular weight salt used is sodium chloride, the safety of the stent is further improved since sodium chloride is a substance which is thoroughly found in a body.

What is claimed is:

1. A stent to be implanted in a body duct comprising:
   a cylindrical stent main body extending in an axial direction and having an opening on each end of the axially extending stent main body; and
   a sustained release coating formed on the surface of the stent main body from which a biologically/physiologically active substance is released; wherein
   said sustained release coating comprises:
   a layer consisting of the biologically/physiologically active substance formed on the surface of said stent main body; and
   a polymer layer formed on said biologically/physiologically active substance layer to cover said biologically/physiologically active substance layer; and
   said biologically/physiologically active substance layer comprises at least one biologically/physiologically active substance;

said polymer layer comprises a vapor or water-permeable polymer, and a water-swellable substance dispersed in said polymer and swollen by absorption of the vapor or the water; and cracks are formed in said polymer layer when said water-swellable substance is swollen by absorbing the vapor or the water, and the biologically/physiologically active substance in said biologically/physiologically active substance layer is released to the exterior of said sustained release coating through said polymer layer.

2. A stent according to claim 1 wherein said stent main body comprises a metal material.

3. A stent according to claim 1 wherein said stent main body comprises a polymer material.

4. A stent according to claim 1 wherein said biologically/physiologically active substance is at least one member selected from a carcinostatic, an immunosuppressive, an antibiotic, an antirheumatic, an antithrombotic, an antihyperlipidemic, an ACE inhibitor, a calcium antagonist, an integrin inhibitor, an antiallergic, an antioxidant, a GPIIb/IIIa antagonist, retinoid, flavonoid, carotenoid, a lipid improving agent, a DNA synthesis inhibitor, a tyrosine kinase inhibitor, an antiplatelet, a vascular smooth muscle antiproliferative agent, an antiinflammatory agent, a biological material, an interferon, and a NO production accelerator.

5. A stent according to claim 1 wherein said vapor or water-permeable polymer constituting the polymer layer is a member selected from silicone polymer, cellulose polymer, polyurethane, polyester, vinyl polymer, acrylic polymer, and thermoplastic elastomer.

6. A stent according to claim 1 wherein said water-swellable substance is a low molecular weight salt having a molecular weight of up to 1000.

7. A stent according to claim 6 wherein said low molecular weight salt is a salt which is found in a body.

8. A stent according to claim 6 wherein said low molecular weight salt is sodium chloride.

9. A stent according to claim 1 wherein said water-swellable substance is a salt that is swollen by absorbing vapor or water in the body after the stent is placed in the body.

10. A stent to be implanted in a body duct comprising:

a cylindrical stent main body extending in an axial direction and having an opening on each end of the axially extending stent main body; and a sustained release coating formed on the surface of the stent main body from which a biologically/physiologically active substance is released; wherein said sustained release coating comprises:

a layer of the biologically/physiologically active substance formed on the surface of said stent main body; and a polymer layer formed on said biologically/physiologically active substance layer to cover said biologically/physiologically active substance layer; and said biologically/physiologically active substance layer comprises at least one biologically/physiologically active substance and an additional component which imparts tackiness to said biologically/physiologically active substance layer;

said polymer layer comprises a vapor or water-permeable polymer, and a water-swellable substance dispersed in said polymer and swollen by absorption of the vapor or the water; and cracks are formed in said polymer layer when said water-swellable substance is swollen by absorbing the vapor or the water, and the biologically/physiologically active substance in said biologically/physiologically active substance layer is released to the exterior of said sustained release coating through said polymer layer.

11. A stent according to claim 10 wherein said stent main body comprises a metal material.

12. A stent according to claim 10 wherein said stent main body comprises a polymer material.

13. A stent according to claim 10 wherein said biologically/physiologically active substance is at least one member selected from a carcinostatic, an immunosuppressive, an antibiotic, an antirheumatic, an antithrombotic, an antihyperlipidemic, an ACE inhibitor, a calcium antagonist, an integrin inhibitor, an antiallergic, an antioxidant, a GPIIb/IIIa antagonist, retinoid, flavonoid, carotenoid, a lipid improving agent, a DNA synthesis inhibitor, a tyrosine kinase inhibitor, an antiplatelet, a vascular smooth muscle antiproliferative agent, an antiinflammatory agent, a biological material, an interferon, and a NO production accelerator.

14. A stent according to claim 10 wherein said vapor or water-permeable polymer constituting the polymer layer is a member selected from silicone polymer, cellulose polymer, polyurethane, polyester, vinyl polymer, acrylic polymer, and thermoplastic elastomer.

15. A stent according to claim 10 wherein said water-swellable substance is a low molecular weight salt having a molecular weight of up to 1000.

16. A stent according to claim 15 wherein said low molecular weight salt is a salt which is found in a body.

17. A stent according to claim 15 wherein said low molecular weight salt is sodium chloride.

18. A stent according to claim 10 wherein said water-swellable substance is a salt that is swollen by absorbing vapor or water in the body after the stent is placed in the body.

* * * * *

UNITED STATES PATENT AND TRADEMARK OFFICE
CERTIFICATE OF CORRECTION

| | | |
|---|---|---|
| PATENT NO. | : 6,833,004 B2 | Page 1 of 1 |
| APPLICATION NO. | : 10/188969 | |
| DATED | : December 2, 2004 | |
| INVENTOR(S) | : Naoki Ishii et al. | |

It is certified that error appears in the above-identified patent and that said Letters Patent is hereby corrected as shown below:

Column 7, line 19, after the word 'like' delete ".". (should read: --use of a material like stainless steel . . .--)

Signed and Sealed this

Ninth Day of January, 2007

JON W. DUDAS
*Director of the United States Patent and Trademark Office*

UNITED STATES PATENT AND TRADEMARK OFFICE
CERTIFICATE OF CORRECTION

PATENT NO. : 6,833,004 B2
APPLICATION NO. : 10/188969
DATED : December 21, 2004
INVENTOR(S) : Naoki Ishii et al.

It is certified that error appears in the above-identified patent and that said Letters Patent is hereby corrected as shown below:

Column 7, line 19, after the word 'like' delete ".". (should read: --use of a material like stainless steel . . .--)

This certificate supersedes Certificate of Correction issued January 9, 2007.

Signed and Sealed this

Sixth Day of February, 2007

JON W. DUDAS
*Director of the United States Patent and Trademark Office*